(12) United States Patent
Liu et al.

(10) Patent No.: US 12,090,243 B2
(45) Date of Patent: Sep. 17, 2024

(54) COMPOSITIONS COMPRISING FLUID GELS FOR TISSUE SEPARATION

(71) Applicant: ALEO BME, INC., State College, PA (US)

(72) Inventors: Chao Liu, State College, PA (US); Chuying Ma, State College, PA (US); Xuedi Yu, State College, PA (US)

(73) Assignee: ALEO BME, INC., State College, PA (US)

( * ) Notice: Subject to any disclaimer, the term of this patent is extended or adjusted under 35 U.S.C. 154(b) by 237 days.

(21) Appl. No.: 17/211,037

(22) Filed: Mar. 24, 2021

(65) Prior Publication Data

US 2022/0305171 A1 Sep. 29, 2022

(51) Int. Cl.
| | |
|---|---|
| A61L 24/00 | (2006.01) |
| A61L 24/04 | (2006.01) |
| A61L 27/26 | (2006.01) |
| A61L 27/52 | (2006.01) |

(52) U.S. Cl.
CPC ......... *A61L 24/0031* (2013.01); *A61L 24/043* (2013.01); *A61L 27/26* (2013.01); *A61L 27/52* (2013.01); *A61L 2300/442* (2013.01); *A61L 2300/802* (2013.01); *A61L 2400/04* (2013.01); *A61L 2400/06* (2013.01)

(58) Field of Classification Search
CPC .... A61L 24/0031; A61L 24/043; A61L 27/26; A61L 27/52; A61L 2300/442; A61L 2300/802; A61L 2400/04; A61L 2400/06
See application file for complete search history.

(56) References Cited

U.S. PATENT DOCUMENTS

| | | | | |
|---|---|---|---|---|
| 5,171,772 A | * | 12/1992 | Hoy | C08G 83/001 524/833 |
| 6,369,117 B1 | * | 4/2002 | Dubief | C08L 33/064 424/70.2 |
| 2002/0061329 A1 | | 5/2002 | Leaderman | |
| 2005/0137356 A1 | | 6/2005 | Hale et al. | |
| 2006/0083721 A1 | * | 4/2006 | Cohen | A61K 31/738 514/54 |
| 2009/0325859 A1 | * | 12/2009 | Ameer | C08G 63/685 524/600 |
| 2013/0165403 A1 | * | 6/2013 | Chu | B01F 23/49 514/54 |
| 2013/0315972 A1 | * | 11/2013 | Krasnow | A01N 25/12 424/618 |
| 2018/0110897 A1 | | 4/2018 | Bush et al. | |
| 2018/0360920 A1 | | 12/2018 | Khademosseini et al. | |
| 2020/0165612 A1 | | 5/2020 | Zhu et al. | |

OTHER PUBLICATIONS

Yuan, Zhize, et al. "Injectable citrate-based hydrogel as an angiogenic biomaterial improves cardiac repair after myocardial infarction." ACS applied materials & interfaces 11.42 (2019): 38429-38439. (Year: 2019).*

Jiang, Zhao, and Timothy Q. Duong. "Methylene blue treatment in experimental ischemic stroke: A mini-review." Brain circulation 2.1 (2016): 48. (Year: 2016).*

Shapiro, Jenna M., and Michelle L. Oyen. "Viscoelastic analysis of single-component and composite PEG and alginate hydrogels." Acta Mechanica Sinica 30 (2014): 7-14. (Year: 2014).*

Ganguly, Sayan, et al. "Polysaccharide and poly (methacrylic acid) based biodegradable elastomeric biocompatible semi-IPN hydrogel for controlled drug delivery." Materials Science and Engineering: C 92 (2018): 34-51. (Year: 2018).*

International Search Report and Written Opinion of the International Searching Authority, mailed Jun. 22, 2022, for corresponding International Application No. PCT/US2022/021301.

* cited by examiner

*Primary Examiner* — Abigail Vanhorn

(74) *Attorney, Agent, or Firm* — Maynard Nexsen PC; John P. Zimmer; Candice Cashman

(57) ABSTRACT

The present disclosure is directed to an injectable composition in form of fluid gel and the use thereof to assist the tissues resection during endoscopic procedures in which it is injected in the tissue of interest to form a cushion for tissue separation. Aspects of the composition can include a gelling agent, a modifier, a salt and water. The composition can be prepared by mixing the gelling agent, modifier, at least one salt and water via continuous stirring to obtain fluid gel solutions, wherein modifier enables the said fluid gel composition to be injected into the submucosal layer of gastrointestinal tissues through endoscopic injection catheter and needle with significantly reduced injection pressure and generate a high and durable cushion for long-lasting tissue raise-up in the submucosal layer, for the application of injection assisted resection procedures.

30 Claims, 12 Drawing Sheets

COMPOSITIONS COMPRISING FLUID GELS FOR TISSUE SEPARATION

FIELD

In general, present disclosure relates to an injectable composition in form of fluid gels and the use thereof to inject in target tissue to generate a cushion assisting endoscopic procedures, for example, in a gastrointestinal (GI) tract of a patient.

BACKGROUND

Endoscopy is a procedure that allows to view and operate on internal organs by using specialized tubular instruments called endoscope, often equipped with light source, camera and surgical tools. It is most commonly used in the gastrointestinal (GI) system to detect or to perform interventions on pathological lesions (including polyps, metaplastic, dysplastic, pre-neoplastic and neoplastic lesions) for diagnostic and therapeutic purposes. In particular, endoscopic mucosal resection (EMR) and endoscopic submucosal dissection (ESD) are the two widely performed GI endoscopic surgical procedures to minimal-invasively remove pathological lesions, especially those sessile, flat, and inaccessible lesions. In EMR, electrosurgical hot snares are used to capture, strangulate and remove target tissue. EMR is mainly used for the removal of small lesions or piecemeal removal of larger lesions between 1.5 cm to 2 cm, while ESD, as a relatively new endoscopic technique, was specifically developed to remove lesions larger than 2 cm, by using electrosurgical knives to create slightly deeper incisions along 5 mm outside the margins of the lesion facilitating an en-bloc resection. In both techniques, the effective lift and separation of diseased tissues from the beneath muscle layers, particularly in cases of large lesions or those in less accessible locations, is essential for a successful surgical procedure. Mechanical separation, such as grasping, pulling, ligation and suction, was originally applied, but often associated with complications, such as perforation, bleeding, and damage to the underlying muscle layer. Therefore, the current clinical approach is to inject a fluid beneath the submucosal layer to physically separate the diseased lesion from mucosal strata and provide a "safety cushion" for the subsequent underlying muscle layers, and increase visibility of the lesion margins before the tissue resection can occur, which is also known as the "inject-and-cut" technique.

The use of submucosal injection is essential for the majority of EMR techniques and especially for a successful ESD, by reducing thermal injury, the risk of perforation and bleeding, while facilitating en-bloc resection. An ideal injection solution should meet the following requirement to have clinical relevance: 1) Biocompatible. The injection solution should be non-toxic with no exogenous pathogens, trigger no or minimal tissue inflammation, induce no tissue damage, and at least not impede the subsequent wound healing, and should be easily eliminated from the body. 2) Submucosal lift and duration. The injection solution must provide maximum submucosal elevation heights, preferably with a steeper and clearer margin and maintain lift duration for the entire surgical procedure. 3) Injectable. The solution must be easily injected to the lesion of interest using standard endoscopic tools. 4) Cost and availability. The injection solution should be easy to produce in a cost-efficient manner and all raw materials be readily available at reasonable cost. 5) Bleeding management/control. The solution preferably possesses intrinsic hemostatic capability. Bleeding is reported as the major complication associated with EMR, and is more commonly seen during and after ESD, occurring in 4.5%-15.5% of cases and the risk increases with lesion size, and the risk of post-procedure bleeding remains problematic. Meanwhile, given any bleeding encountered during the procedure should be controlled expeditiously, the intrinsic hemostatic property of the solution may also reduce procedure time and help relieve the inconvenience caused by the use of endoscopic electro-coagulation tools.

Various injectable materials have been developed for submucosa injection. Saline is the most commonly used solution in endoscopy clinically and considered to be the "gold standard" due to its non-toxicity, low cost, and ease of use. However, it suffers from quick dissipation, and often requires repeated injections resulting in surgical difficulties and higher risk of adverse response. To overcome this limitation, hypertonic (e.g., hypertonic glucose, glycerol, and dextrose solutions) and viscous solutions (e.g., sodium hyaluronate, fibrinogen, gelatin, sodium carboxymethyl starch, hydroxypropyl methylcellulose, and sodium alginate), consisting of charged molecules, and natural/synthetic polymers, are then employed in order to achieve greater lift heights with longer lift duration, but they all have their own advantages and disadvantages. Hypertonic solutions generally could produce higher cushion initially than normal saline, but the elevation duration remains unsatisfied when removing lesions larger than 2 cm and tends to cause tissue damage. Sodium hyaluronate viscous solution (exemplified as the SigmaVisc™ by Hyaltech Ltd, UK and MucoUp by Seikagaku Corp., Japan) is reported to have high submucosal lift with longer duration. However, its application is often limited by its high-cost, high injection pressure, and low availability, and it may potentially facilitate cancer cell growth associated with higher risk of recurrence. Fibrinogen solution is available at reasonable price and has a high viscosity to produce a long-lasting submucosal elevation, but it is suffered from the risk of disease transmission. The application of hydroxypropyl methylcellulose is also limited by the tissue damage it may cause after submucosal injection.

The solution with a high viscosity or the solution capable of forming of a gel after injection is generally associated with better elevation performance, because viscous solution and gel have less tendency to spread out or be absorbed by surrounding tissues. Injectable gels, specifically polysaccharide gels preferably with shearing-thinning properties, such as the gellan gum (exemplified as the Orise™ Gel by Boston Scientific) and the ionic-crosslinked alginate gels have been developed for prolonged submucosa elevation. However, the high viscosity of solution compromises its injectability, which makes the solution hard to flow through or even has the risk of obstructing the endoscopic injection device. Therefore, the viscosity of solution needs to be precisely tuned to balance its elevation performance and injectability, but currently limited approach is available that provides flexibility to improve elevation without affecting injectability. "High pressure" generating device (described in WO2011103245 by Cook Medical) has been designed to assist the injection of highly viscous solution but may introduce risk of tissue damage and add inconvenience to the endoscopic procedures. Another way to address this issue is the use of purified inverse thermosensitive polymers (exemplified as the LeGoo-endo™ disclosed in WO2009070793) that remain as liquid at low viscosity during injection and enable in situ gelling to display high viscosity after injected into target tissue where the solution reaches body temperature. Although with elevation improved, the inverse thermosensitive polymers may reach body temperature before they arrive at the target tissue, thereby gelled and clogged in the endoscopic tube/catheter, greatly compromising their injectability.

In view of this, inverse thermosensitive polymer with a concentration lower than its critical gelling concentration (CGC), thereby maintaining the solution at low viscosity even at body temperature was designed for EMR injection, exemplified by Eleview® of Aries Pharmaceuticals, Inc (disclosed in WO2015075024). The main component of the Eleview® solution is poloxamer 188, an inert and non-degradable polyether that forms into an emulsion in water with the aid of surfactants. After injection, the solution turns into viscous product to provide immediate and long-lasting elevation up to 60 minutes, however, bubbles may be easily formed when using Eleview® thereby obscuring the endoscopic view, and its unknown clearance path in the body may be another concern. More importantly, a recent report on the use of Eleview® for EMR and ESD procedures on 11 patients showed that Eleview® is safe and effective for EMR procedures, however, the lift duration only lasts for average of 12.5 min (range: 10-15 min) in human, which is much shorter than the claimed 60 min lift duration in pig models, thus is mostly inadequate for completion of ESD procedures which usually last 60-140 min. Multiple injections are needed for ESD procedures when using Eleview®. The endoscopist graded the ESD procedures using Eleview® on 3 out of 4 patients as moderately difficult and the procedures may be very costly ($81 per 10 mL). The huge discrepancy between pig models and human trials may hint that the use of low concentration of poloxamer 188 may not be able to form a cushion with sufficient viscosity to maintain long-lasting lift in humans. However, simply increasing concentrations to increase viscosity would result in increased injection pressure thus reducing injectability of the injectable solutions through endoscopic tools. Such conflict in balancing injection pressure and viscosity constitutes a significant challenge in developing ideal injectable solutions for clinical EMR and ESD procedures.

Although encouraging progress has been made, there are no current submucosal injection solutions in forms of liquid, gels, and emulsions, can directly address all the above requirements and enable convenient uses both in EMR and ESD in a single product. Therefore, there is an urgent need to provide a solution to assist the endoscopic procedures, particularly in EMR and ESD, that is biocompatible, cost-effective and readily available, easy to inject while providing high and long-lasting submucosal elevation and is preferably hemostatic.

SUMMARY

Generally, the present disclosure is directed to injectable compositions in form of fluid gels, the methods of preparing such compositions, and the use thereof to inject into human to form a cushion in the endoscopic procedures, preferably in the polypectomy, EMR and/or ESD procedures.

The present disclosure provides injectable compositions, wherein said injectable compositions comprise at least one gelling component that is long-chain and hydrophilic polysaccharides, proteins or their derivatives, at least one salt as a source of monovalent or multivalent cations or anions, at least one modifier, and water.

The present disclosure provides injectable compositions, wherein said injectable composition is formulated in forms of fluid gels, a type of structured liquid that flows. In detail, wherein said fluid gel is comprising a suspension of gelled particles that may weakly held together via inter-particle interactions as a viscous solution at a flowable, hard-to-flow, or even non-flowable state and the inter-particle interactions may be easily disrupted when agitated, shear-stressed or otherwise disturbed, displaying a thixotropic behavior or shear-thinning behavior.

The present disclosure provides injectable fluid gel compositions, wherein said injectable compositions comprise at least one gelling component that is long-chain and hydrophilic polysaccharides, proteins or their derivatives, characterized by their property of forming viscous dispersions and gels when dispersed in water.

The injectable fluid gel composition includes at least one modifier, wherein said modifier can impact on the gelation of the gelling component, by partially blocking or bridging the interactions between the gelling component chains during the formation of gelled particles, or the interactions between gelling component chains and salts, or the interactions between adjacent particles, or between particles and salts. It at the same time imparts flexibility to tune composition properties such as hydrophobicity in order to intricately balance the tissue elevation performance and the fluid gel injectability.

The present disclosure provides an injectable fluid gel composition includes at least one gelling component and at least one modifier, and wherein said gelling component and modifier are compatible in water, which are miscible at molecular level or are easily dispersible in water.

The present disclosure provides an injectable fluid gel composition includes at least one salt as a source of monovalent or multivalent cations or anions. The introduction of salt in some embodiments may provide ions to induce the formation of gelled particles. In some embodiments, the salt may be used for the modulation of solution osmotic pressure or the ionic strength. In some embodiments, organic salts may be added to adjust the composition pH, or the cross-linking capability of the gelling agents or between gelled particles.

In some aspect, the injectable composition may include additional agents, such as a pharmaceutically acceptable coloring agent, to assist the identification of submucosal layer, and the lateral margin of target lesions.

According to certain aspects, the injectable composition may include therapeutic agents such as rebamipide to aid in wound healing or photosensitizers such as hematoporphyrin, Mesotetra (hydroxyphenyl) chlori (mTHPC), motexafin lutetium, padoporfin etc. to treat cancers via photodynamic therapy.

Additionally or alternatively, the injectable composition may have intrinsic hemostatic capabilities, which may be derived from the gelling component, the modifier, the salt or a combination thereof.

The present disclosure also contemplates methods for preparing the injectable fluid gel compositions. For instance, one example method can include adding the salt to a mixture including the gelling component and modifier under continuously stirring to obtain injectable fluid gels solution. Another example method can include first heating a mixture of the salt, the gelling component, and the modifier, followed by cooling under continuously stirring to generate injectable fluid gels solution.

In another aspect, the present disclosure also provides a method to administer said injectable composition to a human for use as an elevating or cushioning agent in endoscopic procedures. As one example for illustration, the method can include transferring the injectable composition into a container, preferably a syringe wherein the composition remains in the form of a fluid gel prior to injection; and injection of the said composition leads to accumulation of the fluid gel at a tissue site, wherein said composition turns into viscous gel or gelled product (e.g., due to reduced shear stress at the tissue site) to provide a cushion.

One of the objectives of the present disclosure is to provide injection compositions with low injection pressure and/or improved tissue elevation performance which can provide advantages for performing endoscopic procedures such as EMR and/or ESD procedures. The objective is achieved in example embodiments of the present disclosure by compositions which include a modifier to tune fluid gel properties to adjust the injection pressure and maintain a prolonged cushion performance.

Another objective of the present disclosure is to provide injectable compositions with hemostatic properties for bleeding control during or after the endoscopic procedure.

BRIEF DESCRIPTION OF THE DRAWINGS

FIG. 11A depicts representative images of the whole blood clotting, and FIG. 11B depicts a comparison of the clotting time (n=5).

Figure 1:
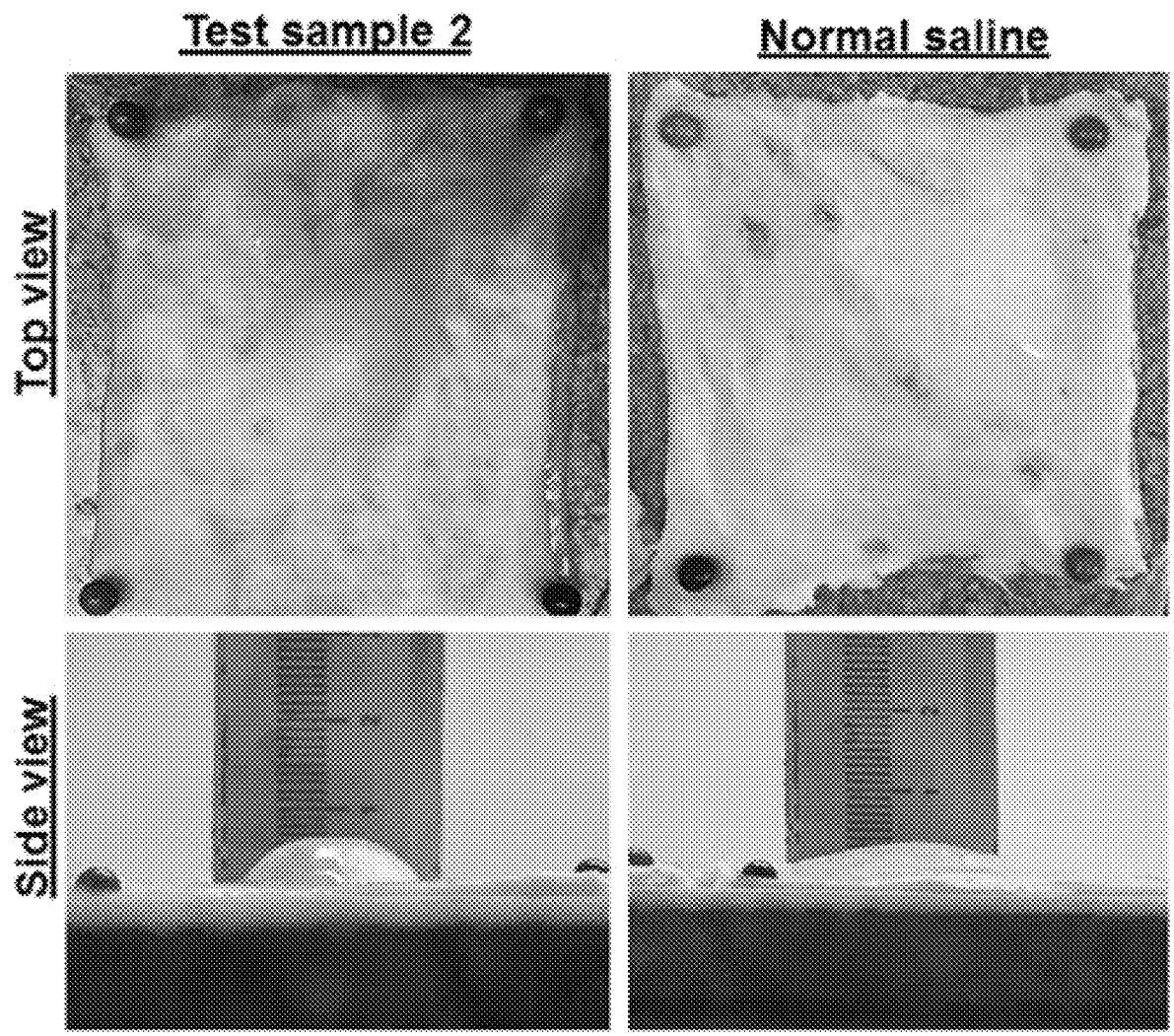
FIG. 1 illustrates morphology of the cushion in the submucosal layer of colon sample after injecting 1 mL of test sample 2 (TS-2) compared to injecting 1 mL of normal saline.

The present disclosure may be better understood with reference to the following non-limiting examples with reference to the foregoing drawings.

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present disclosure. Numerous modifications and adaptations will be readily apparent to those of skill in the art without departing from the spirit and scope of the invention.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

The present disclosure provides injectable compositions, the methods of preparing such compositions, and the use thereof to inject into a human tissue to form a cushion in endoscopic procedures, preferably EMR and/or ESD procedures. The injectable compositions are biocompatible, cost-effective and readily available. The said compositions are easy to inject due to its low injection pressure while providing a high, long-lasting submucosal elevation and hemostatic function.

The present injectable composition in forms of fluid gels comprising at least one gelling component, at least one modifier, at least one salt, optionally a coloring agent or therapeutic agent, and water, surprisingly is capable of forming a high and long-lasting cushion after submucosal injection to assist the endoscopic procedures, preferably EMR and/or ESD procedures.

As well known in the art, increasing solution's resistance to flow (viscosity) and/or its capacity to form entangled networks (gel formation) after submucosal injection are key to achieve high and long-lasting elevation performance. Therefore, long-chain biopolymers (polysaccharides and proteins), especially polysaccharide, as well-known thickening and gelling agents commonly seen in food and cosmetic products, when applied in submucosal injection are usually prepared at high concentrations (13) or is prepared in forms of entangled networks with the addition of cross-linkers (9), to induce a significant increase in viscosity. However, the use of polysaccharide alone or in combination with crosslinkers such as a salt does not fully satisfy the EMR/ESD's needs, since it has been a challenge to balance reasonable injectability while maintaining sufficient lifting performance by using polysaccharide alone or in combination with crosslinkers in forms of either solution or bulk gels.

The discovery that polysaccharides can be sheared during gelation to produce a fluid gel structure, that is, a suspension of gelled particles in non-gelling continuous medium, may widen the potential application of these gelling agents in submucosal/mucosal injection areas. Fluid gels have wide variations in performance and rheological properties, distinct from viscous liquid and crosslinked gels described above, depending on the choices of biopolymers (e.g., polysaccharide, protein type, or mixed components), the concentrations of biopolymers used, the choices of salts and the concentrations of salts if gelation is ion mediated, as well as the processing conditions (directly related to the particle size and degree of particle interaction) (14). One of the most attractive rheological properties of fluid gels for endoscopic applications is their thixotropic and/or shear-thinning behavior (15, 16), characterized by the decrease in viscosity when subjected to critical shear stress, and by their ability to recover its viscosity after removal of the shear stress.

The thixotropic and shear-thinning behavior may be explained as follows: When the gel fraction in fluid gels is high enough, the gel particles interact and even closely pack to form entangled network with or without crosslinkers, thereby generating viscous but flowable fluid gels, hard-to-flow fluid gels or even non-flowable fluid gels. The viscous fluid gels undergo shear-thinning transformation due to the disruption of particular interactions under shear stress such as during injection, thus enabling injection through an endoscopic injection catheter and needle. After injection force or shear stress removal, the particular interactions are re-established and the fluid gels return to viscous state or hard-to-flow state or non-flowable state.

In the case of submucosal lifting, it was surprisingly discovered that the viscous fluid gel composition comprising gelling agent alone or gelling agent with the crosslinker become less flowable, hard-to-flow or even non-flowable once injected into the confined submucosal layer (space) depending on the fluid gel concentrations. As a person skilled in the art will recognize, such results were unexpected and unobvious when compared to injecting a thixotropic material into an unconfined space. Such unexpected viscosity increases or thickening effect instead of simply returning to the original viscous state of the thixotropic fluid gels favor tissue elevation, thus is considered as a significant advantage in endoscopic procedures. We reasoned that in the confined submucosal space, the interaction between gel particles and the interaction between gel particles and surrounding tissue are enhanced, leading to enhanced viscosity. Although the mechanism for such unexpected viscosity transformation in submucosal layer is not fully understood, but this interesting phenomenon of fluid gels suggests that the fluid gels may serve as a good candidate for submucosal injection in EMR or ESD procedures. However, in order to maintain a good tissue elevation, the concentration of fluid gel comprising gelling agent alone or with the crosslinker has to be high enough, which results in a poor injectability of the viscous fluid gel composition through an endoscopic injection tool comprising an endoscopic catheter and an endoscopic needle. Although decreases in solution viscosity by decreasing fluid gel concentrations may improve the injectability but inevitably sacrificing the tissue elevation capability or resulting in short tissue elevation time.

Modifiers in accordance with the present disclosure may impact gelation of the gelling component by partially mediating (blocking or bridging) the interactions between the gelling component chains during the formation of gel particles, the interactions between gelling component polymer chains and salts (or crosslinkers) during the formation of gel particles, the interactions between adjacent particles, and/or the interactions between particles and salts were introduced to the fluid gel composition. It was surprisingly discovered that example fluid gel compositions in accordance with the present disclosure, can include one or more modifiers, which act to partially or fully mediate the interactions between gelling component polymer chains and salts (or crosslinkers), the interactions between adjacent particles, and/or the interactions between particles and salts. In this manner, embodiments of the disclosure can display reduced viscosity, and thereby the injection pressure. It was also interestingly discovered that the fluid gels become more viscous or thickened once injected into the confined mucosal or submucosal layer, which provides for long-lasting tissue lift. Without being bound to any particular theory, it was reasoned that in the confined submucosal space, the modifier may modulate the fluid gel properties, such as hydrophobicity, charge distribution, and/or presence of functional groups, leading to enhanced interactions between adjacent particles, enhanced interactions between particles and salts, and/or enhanced interactions between particles and submucosal extracellular matrix. Such fluid gel composition can provide a significant advantage as it addresses the aforementioned challenge in developing EMR solutions by enabling easier injection while maintaining higher and/or longer-lasting submucosal cushion in endoscopic applications to better facilitate the following endoscopic resection and/or dissection procedures.

Therefore, fluid gel compositions in accordance with the present disclosure preferably remain in a flowable state before and during injection through an endoscopic catheter and needle, at temperatures ranging from room temperature to body temperature.

It was also surprisingly discovered that example fluid gel compositions of the present disclosure, such as those including at least one gelling component, at least one modifier, at least one salt and water, can display decreased injection pressure by the introduction of the modifier, while also maintaining long-lasting tissue elevation (e.g., compared to saline solution) after injection into mucosal or submucosal tissues.

Aspects of example fluid gel compositions can include an injection pressure of no greater than 50 psi, preferably below 30 psi, and more preferably below 20 psi when using an injection tool that is commonly used in endoscopic procedures, such as an endoscopic injection needle with a needle diameter at gauge 21-26, connected to a catheter with a working length up to 2700 mm and a channel size smaller than 2.8 mm. For instance, in some embodiments, the fluid gel composition can have an injection pressure in the range from 50 psi to 2 psi when using an endoscopic injection needle as disclosed herein, such as an injection pressure in the range from 40 psi to 5 psi, from 30 psi to 5 psi, or from 20 psi to 10 psi.

According to the disclosure, example fluid gel compositions can display a shear-thinning behavior, where fluid viscosity decreases under shear strain, with a shear-thinning index between 1 and 20, and preferably between 2 and 12. In some implementations, the method for determining the shear-thinning index is defined by ASTM standard D2196. For example, the shear-thinning index can be defined as a ratio of the apparent viscosities at a low rotational speed and the apparent viscosities at a high rotational speed, and the said high rotational speed is 10 times as much as the low rotational speed.

According to the disclosure, example fluid gel compositions can include one or more hemostatic components.

Component (A): Gelling Component

According to the disclosure, the composition includes at least one gelling component such as polysaccharide, which could be used to prepare fluid gels by applying a sufficiently energetic flow field to biopolymer solution when the biopolymer is undergoing conformation transition and consequent aggregation. Wherein said gelling component is preferably biocompatible and hemostatic. It includes thermo-reversible and thermo-irreversible polysaccharides which can be linear or branched, ionic or neutral, and purely natural or modified. Non-limiting examples of the gelling agents that are used for fluid gel preparation include alginate, xanthan gum, k-carrageenan, gellan gum, guar gum, locust bean gum, pectin, carboxymethyl starch, hydroxyethyl starch, chitosan and agarose. Among them, a preferred example is alginate.

In some embodiments, the composition may also include proteins and their derivatives as the at least one gelling component, which could be used to prepare fluid gels by applying a sufficiently energetic flow field to biopolymer solution when the biopolymer is undergoing conformation transition and consequent aggregation. Wherein said proteins are preferably biocompatible. Non-limiting examples of the proteins include gelatin and whey protein.

Alginate is a natural linear polysaccharide extracted from brown seaweed and is a heteropolymeric chain composed of two kinds of monomers, poly-β-mannuronic acid (M) and poly-α-L-guluronic acid (G). The addition of divalent cations, such as $Ca^{2+}$, $Mg^{2+}$, $Zn^{2+}$, and $Ba^{2+}$, and the binding of said divalent cations to the alginate chains, preferentially to the G block of alginate, gives rise to the formation of gels. Alginate fluid gel could be obtained by directly introducing the active form of divalent cations into the alginate solution under shear. Moreover, alginate has been used as hemostatic agents in wound dressing, primarily by accelerating fibrin formation and via acting as calcium donors if crosslinked by calcium ions for thereby platelet activation and whole blood coagulation (17).

Alginate includes alginic acid and its monovalent salts, such as sodium alginate, potassium alginate, propylene glycol alginate, and ammonium alginate. Among them, a preferred example is sodium alginate and potassium alginate.

Alginate extracted from different sources differ in M and G contents, and the M/G ratio greatly affects the alginate's gel capability and the gel strength. In some embodiments, the M/G ratio of alginate may range from 0.45 to 3.35, preferably from 0.6 to 2.0, more preferably from 0.8-1.6.

In some embodiments, the fluid gel composition may comprise 0.05 to 6.5 w/v % sodium alginate or preferably 0.1% to 3.6 w/v % sodium alginate, or more preferably 0.125% to 1 w/v % sodium alginate.

In some embodiments, sodium alginate described herein may have a viscosity (at 1 w/v %, 20° C.) of 5 to 1500 cP, preferably from 100 cP to 700 cP, more preferably from 300 to 600 cP.

Component (B): Modifier

According to the disclosure, the fluid gel composition includes at least one modifier, which is compatible with the gelling component (A) and is capable of affecting the gelation process of the gelling component (A). The said modifier can affect the inter-polymer chain interactions during the formation of gelled particles and/or can impact the inter-particle interactions. Wherein said modifier is preferably biocompatible and hemostatic. The said modifier includes hydrophilic synthetic polymers, hydrophilic natural polymers, and amphiphilic polymers. Non-limiting examples of hydrophilic synthetic polymers include poly (ethylene glycol) (PEG), polyvinyl alcohol (PVA), polyacrylic acid (PAA), poly (methacrylic acid), and hydrophilic polyesters, and non-limiting examples of amphiphilic polymers include the poly(ethylene oxide) (PEO)-poly (propylene oxide) (PPO)-poly(ethylene oxide) (PEO) block copolymer and amphiphilic polyesters. The said modifier also includes natural oligomers and/or low molecular weight polysaccharides. Non-limiting examples include oligoguluronate, the guluronate block extracted from alginate (18), oligomannuronate (the mannuronate block extracted from alginate), the oligouronate (the urinate block extracted from pectin (19)), and the low molecular weight chitosan.

Among them, a preferred modifier is the fully synthetic polyester with abundant pendant groups, wherein said synthetic polyesters are synthesized via the polycondensation of one highly reactive polycarboxylic acid, at least one hydrophilic diol and/or with at least one hydrophobic diol and/or at least one amphiphilic diol. The said synthetic polyester is easy to synthesize and could be hydrophilic or amphiphilic depending on what diols are introduced. It also imparts flexibility to tune composition properties such as hydrophobicity by varying the monomers to react with tricarboxylic acid or by adjusting the ratios of hydrophobic and hydrophilic diols, thereby intricately balancing the elevation performance and the injectability. The said synthetic polyester also possesses abundant pendant groups, such as carboxyl groups, which may impart strong calcium-binding capabilities to allow the delivery of more calcium ions, a well-known hemostatic agent, into the submucosal layer, thus decreasing the blood coagulation time during endoscopic resection and reducing the risk of after-procedure bleeding. In addition, the abundant free pendant groups may impart mucoadhesive properties to the composition via the formation of hydrogen bonding and electrostatic bonding between the pendant groups and the surrounding tissues. Lastly, the high reactivity of tricarboxylic acid allows the introduction of charged moieties or other functionality (e.g., antioxidant properties and antimicrobial properties,) and imaging capabilities (e.g., fluorescent imaging and photoacoustic imaging) or light absorption capability into the polymer by reacting it with a wide choice of monomers.

In some embodiments, the said modifier is synthesized by reacting highly reactive polycarboxylic acid, at least one hydrophilic diol and/or with at least one hydrophobic diol and/or at least one amphiphilic diol, wherein said highly reactive polycarboxylic acid possesses multiple reaction sites for polymer chain elongation and displays valuable pendant groups for enhanced interaction with the gelling component, the salt, and/or the surrounding tissues. The said polycarboxylic acid may be tricarboxylic acid and/or tetracarboxylic acid or combination thereof includes but not limited to aconitic acid, propane-1,2,3-tricarboxylic acid, agaric acid, citric acid, isocitric acid, trimesic acid, furantetracarboxylic acid, Biphenyl-3,3', 5,5'-tetracarboxylic acid, BI(cyclopropane)-2,2',3,3'-tetracarboxylic acid, 1,2,3, 4-Butanetetracarboxylic acid, 1,2,3,4-Cyclobutanetetracarboxylic acid, and (+)-(18-Crown-6)-2,3,11,12-tetracarboxylic acid.

In some embodiments, the said modifier is synthesized by reacting highly reactive polycarboxylic acid with at least one hydrophilic diol. The at least one hydrophilic diol that used in the said modifier syntheses contributes to the formation of polymer chain with tricarboxylic acid, enables the dissolution or homogenously dispersion of resultant polymer modifier in water. Non-limiting examples of hydrophilic diols include 1,4-butanediol, 1,6-hexanediol, poly (ethylene glycol) (PEG), 1,2-propanediol-sebacate, and poly(vinyl alcohol), and any combination thereof.

In some embodiments, the said modifier is synthesized by reacting highly reactive polycarboxylic acid with at least one hydrophilic diol as described above and/or at least one hydrophobic diol. The at least one hydrophobic diol that used in the said polymer modifier syntheses can modulate the polymer's hydrophobicity, which favoring prolonged submucosal elevation by preventing the diffusion of water. Non-limiting examples of the hydrophobic diol include aliphatic diols at different carbon length such as 1,8-octanediol, 1,10-decanediol, poly(propylene glycol) (PPG), 1,12-dodecanediol, polycaprolactone (PCL) diol and polylactide (PLA) diols and any combination thereof.

In some embodiments, the said modifier is synthesized by reacting highly reactive polycarboxylic acid with the at least one amphiphilic diol such as PEG-PPG-PEG copolymers.

In some embodiments, the molar ratio of hydrophilic diol to hydrophobic diol may range from 10:0 to 0:10, preferably from 9:1 to 5:5.

In some embodiments, positive charged moieties can be introduced in the said modifier syntheses to adjust the charge distribution and charge density of the resultant polymer chain. Non-limiting examples include positively charged amino acid (such as lysine and arginine), N-methyldiethanolamine (MDEA), or any combination thereof.

In some embodiments, phosphate-containing diols can be used in the said modifier syntheses to adjust the charge density and modulate the ionic interaction of resultant polymer to the gelling component (A). Non-limiting examples include phosphorylated amino acids (such as phosphoserine, phosphothreonine, and phosphotyrosine), β-glycerophosphate, or any combination thereof.

In some embodiments, the molecular weight of said modifier may range from 500 to 20,000 Da, preferably 600 from 15,000 Da, and more preferably from 800 to 1,0000 Da.

In some embodiments, the fluid gel composition comprises 0.001 to 10 w/v % modifier or preferably 0.05% to 8 w/v % modifier, or more preferably 0.25% to 5 w/v % modifier.

Component (C): Salt

According to the disclosure, the injectable fluid gel composition includes at least one salt as a source of monovalent, divalent, or multivalent cations and/or anions, wherein said at least one salt is compatible with the gelling components and the modifier, and is preferably biocompatible and hemostatic.

In some embodiments, the introduction of divalent cations mediates the gelation of Component (A), such as $Ca^{2+}$, $Sr^{2+}$, $Zn^{2+}$, $Mn^{2+}$, $Co^{2+}$, $Ni^{2+}$, $Cd^{2+}$, and $Ba^{2+}$, which display high affinity to Component (A), such as alginate polymer chains. Among all cations, $Ca^{2+}$ is preferred, from the perspective of effectively mediating the gelation of sodium alginate and its role in hemostatic process. Non-limiting examples of calcium salts include calcium chloride, calcium lactate, calcium gluconate, calcium tetraborate, calcium citrate, calcium sulfate, calcium glycerophosphate, and dibasic calcium phosphate.

In some specific embodiments when alginate is used as Component (A), the concentrations of the calcium salt may range from 0.006 to 0.9 w/v %, preferably from 0.01 to 0.4 w/v %, more preferably from 0.014 to 0.12 w/v %.

In some embodiments, monovalent cations or all anions, dissolved in water that are compatible with the composition may be added to adjust the osmotic pressure or the ionic strength of the composition. Monovalent cations suitable for the composition include but not limited to sodium salts and potassium salts and any combination thereof, while anions that may be suitable for the composition include but not limit to chlorides, phosphates, carbonate, bicarbonates, and sulfates and any combination thereof. Among all cations, sodium salt is preferred. Non-limiting examples of sodium salts include sodium chloride, sodium bicarbonate, sodium phosphate dibasic, sodium sulfate, sodium gluconate, sodium lactate, sodium citrate, sodium glycerophosphate.

In some embodiments, organic salts or its acid form that are compatible with the composition may be added to adjust the composition pH, ionic strength, or the crosslinking capability of Component (A). Organic salts or its acid form may include but not limit to citrate or citric acid, maleate or maleic acid, glutamate or glutaric acid, oxalate or oxalic acid, lactate or lactic acid, gluconate or gluconic acid as well as tartrate or tartaric acid, or any combination thereof.

The above Component (C) may be used singly or as a combination of two or more. For example, calcium chloride at certain concentration can be added to mediate the gelation of Component (A), while sodium chloride at certain concentration can be added to adjust the osmotic pressure of the resultant composition.

Component (D): Water

According to the disclosure, the above Components are dissolved in water as Component (D), and the said water is preferably purified water, or distilled water, or deionized water, free of pathogens and free of endotoxin.

Other Components

In some embodiments, the composition may additionally comprise one or more other components, such as coloring agents, preservatives, defoamer, stabilizers, antioxidants, photosensitizer or therapeutic agents, which are compatible with the composition and are biocompatible for biomedical uses.

In some aspects, the composition may additionally comprise coloring agents to assist the identification of submucosal layer, and the lateral margin of target lesions. The said coloring agents include indigo carmine, methylene blue (MB), lugol iodine, toluidine blue, cresyl violet, congo red, phenol red, indocyanine green (ICG) or any FD&C color additive listed in the US FDA color additive active inventory for food and internal drug uses. The addition of indocyanine green (ICG), in some aspects, may also contribute to the fluorescent and photoacoustic imaging-assisted resection of pathological lesions.

In some aspects, the composition may additionally comprise fluorescent dyes to assist the identification of submucosal layer via fluorescent imaging, wherein said fluorescent dyes include but not limit to xanthene derivatives (such as fluorescein and rhodamine), cyanine derivatives (such as cyanine, indocyanine green (ICG)), quantum dots, and a class of small molecule fluorescent dyes synthesized by reacting citric acid (CA) and amine-containing compounds, such as different amino acids. In some instances, the said fluorescent dye is CA-Cys, a fluorescent dye synthesized by reacting citric acid and cysteine, wherein said CA-Cys when added into the composition not only provide strong fluorescence enabling fluorescence imaging but also may function as crosslinker for alginate as the gelling component.

In some other aspects, the composition may additionally comprise phosphorescent materials to assist the identification of submucosal layer via phosphorescence imaging, wherein said phosphorescent materials include but not limit to zinc sulfide, strontium aluminate, or organic phosphorescent materials.

In some other aspects, the composition may comprise additional therapeutic agents to promote the subsequent wound healing after the endoscopic procedure, such as the epinephrine to further prevent post-procedure bleeding, the proton pump inhibitor or the Rebamipide to promote wound healing while prevent the formation of ulcers after the stomach resection procedure, the chemotherapeutics to prevent cancer recurrence, the antibiotics to prevent infections, or anti-inflammatory agents to prevent post-procedure inflammation. In some aspect, the therapeutic agents may be photosensitizers such as hematoporphyrin, Mesotetra (hydroxyphenyl) chlori (mTHPC), motexafin lutetium, padoporfin etc. to treat cancers via photodynamic therapy.

Method to Prepare the Composition

The present disclosure also includes the method to prepare the injectable fluid gel compositions, in some instance, wherein the method comprising the preparation of the fluid gel composition; sterilization of the composition; transferring the solution into a syringe wherein the composition remain in forms of fluid gels prior to injection; and injection of the composition in forms of fluid gels from syringe through an endoscopic needle to targeted tissue, wherein the composition turn into viscous gel or weak gel like product to provide a cushion, such as the submucosa fluid cushion.

In some embodiments, the fluid gel composition was prepared by directly mixing Component (A), (B), (C) and optionally the said other components directly in water under continuously stirring (e.g., using a jacketed pin-stirrer or a magnetically stirrer) to obtain injectable fluid gels solution.

In some other embodiments, salt solution as Component (C) was added to the mixture of Component (A), (B) and optionally the said other components under continuously stirring (e.g., using a jacketed pin-stirrer or a magnetically stirrer) to obtain injectable fluid gels solution.

In some other embodiments, salt solution as Component (C) was mixed with polymeric modifier as Component (B) first, then the mixture was added to Component (A) and optionally the said other components under continuously stirring (e.g., using a jacketed pin-stirrer or a magnetically stirrer) to obtain injectable fluid gels solution.

In some other embodiments, the fluid gel composition was prepared by first mixing Component (B) with other components, such as the coloring agent, then adding Component (A) to form a homogeneous solution, followed by adding salt solution as Component (C) under continuously stirring to obtain injectable fluid gels solution.

In some other embodiments, the fluid gel composition was prepared by heating of the Component (A), (B), and (C) mixture in water, followed by gradual lowering the mixture temperature under continuously stirring to obtain injectable fluid gels solution.

In some other embodiments, the fluid gel composition was prepared by heating of the Component (A) and (B) mixture in water, followed by gradual lowering the mixture temperature and then adding component (C) under continuously stirring to obtain injectable fluid gels solution.

In some other embodiments, the fluid gel composition was prepared by heating of the Component (A) in water, followed by gradual lowering the solution temperature and then adding component (B) and (C) under continuously stirring to obtain injectable fluid gels solution.

In some embodiments, the composition may be provided in a form of liquid with all components mixed, sterilized and pre-filled in a syringe.

In some other embodiments, the composition may be provided in a form of liquid with all components mixed, sterilized and pre-filled in an ampoule.

In some other embodiments, the composition may be provided in a form of liquid with all components mixed, pre-filled in a syringe or an ampoule, and terminal sterilized.

In some other embodiments, the composition may be provided in a form of lyophilized powders with all the components mixed, sterilized and filled in one container, in combination of sterilized water in another container. Sterilized water is transferred by syringe to dissolve the lyophilized powder before administration in endoscopic procedures.

In some other embodiments, the composition may be provided in a form of two-part formulation, where part (1) of the formulation may be provided in a form of liquid or lyophilized powders with gelling agent included, sterilized and filled in one container, while part (2) of the formulation may be provided in a form of liquid or lyophilized powders with modifier and salt mixed, sterilized and filled in another container. Premixing of the two parts of the formulation in water will be performed before administration in endoscopic procedures.

In some other embodiments, the composition may be provided in a form of two-part formulation, where part (1) of the formulation may be provided in a form of liquid or lyophilized powders with gelling agent and modifier mixed, sterilized and filled in one container, while part (2) of the formulation may be provided in a form of liquid or lyophilized powders with salt included, sterilized and filled in another container. Premixing of the two parts of the formulation in water will be performed before administration in endoscopic procedures. The composition is desired to be sterilized according to any suitable method, which is not particularly limited. Non-limiting examples includes gamma irradiation, ethylene oxide sterilization, UV irradiation, electron beam sterilization, filtration and autoclaving.

Method to Use the Composition

The present disclosure also provides a method to use the composition for an endoscopic procedure, said method comprising the injection of the viscous fluid gel composition that is remained as a viscous fluid gel state after entering the target tissues of a human, preferably into submucosal layer of a GI tract, and preferably become an even more viscous gel after entering the target tissues. More in detail, the fluid gel composition is injected to the target tissues using an endoscopic injection tool in order to form a cushion to assist the subsequent resection or dissection procedure, wherein said endoscopic injection tools comprises a tube with an effective length of 1000 mm or more, preferably from 1500 to 2500 mm and a standard endoscopic injection needle with the diameter between 21-26 gauge.

In some embodiments, the method to use the composition may include adding water into the composition in a form of lyophilized powders, mixing all components thoroughly to obtain homogeneous solution, transferring the solution to a syringe that can be connected to an endoscopic injection tool, injecting the composition solution to the target tissue using the endoscopic injection tools in order to form a cushion to assist the subsequent resection or dissection procedure, wherein said endoscopic injection tools comprises a tube with an effective length of 1000 mm or more, preferably from 1500 to 2500 mm and a standard endoscopic injection needle with the diameter between 21-26 gauge.

In some other embodiments, the method to use the composition may include mixing the two parts of the formulation thoroughly to obtain homogeneous solution, transferring the solution to a syringe that can be connected to an endoscopic injection tools, injecting the composition solution to the target tissue using the endoscopic injection tools in order to form a cushion to assist the subsequent resection or dissection procedure, wherein said endoscopic injection tools comprises a tube with an effective length of 1000 mm or more, preferably from 1500 to 2500 mm and a standard endoscopic injection needle with the diameter between 21-26 gauge.

In a preferred application of the disclosures, the composition is injected in target tissues of a human through an endoscopic needle to lift the target tissue layer, wherein the said target tissue layer includes submucosal layer, mucosal layer, and epithelial layer. The targeted and preferred application site of the said composition includes esophagus, stomach, duodenum, small intestine, cecum, colon and rectum along the GI tract.

In addition, embodiments of the disclosure may also be applied to numerous procedures other than the GI endoscopic procedures, wherein said procedures include oral procedures, urologic procedures, plastic surgeries, or open invasive surgeries, where tissues separation is required.

Advantages of the Present Disclosure

In view of the preceding disclosure, example embodiments can provide one or multiple advantages compared to prior compositions. These advantages can include the viscous fluid gel composition: displaying a thixotropic behavior or shear-thinning behavior during injection; remaining in a flowable state before and during injection for easy injection; setting into a more viscous fluid gel or a cushion following injection; and displaying in a less flowable, hard-to-flow or even non-flowable state once injected into the confined submucosal layer within a 1-15 min for long-lasting tissue elevation.

A further advantage of example embodiments can include modifying the injection pressure so as to be within a suitable range, preferably less than 20 psi, by adjusting the proportion of component (A) to the component (B).

A further advantage of example embodiments can include modulating the gelation capability of component (A), the viscosity and/or hemostatic properties of the resultant composition, or a combination there of by adjusting the proportion of component (A) to the component (C).

The following examples demonstrate aspects of embodiments of the present disclosure. These examples are not meant to limit embodiments solely to such examples herein, but rather to illustrate some possible implementations.

EXAMPLES

Example 1 Composition 1 Preparation

Test samples (TS) 1-5 in Table 1 were prepared by varying the ratio of sodium alginate (Kimica Corporation) as the Component (A) to calcium chloride as the Component (C). Specifically, to prepare the test samples, sodium alginate and modifier xxy84 (illustrated in Example 3) were dissolved in suitable vessels using deionized water. Then, calcium chloride solution was added dropwise and continuously mixed under stirring to obtain a homogeneous and viscous fluid. Methylene blue may be added to TS 1-5 at a concentration of 0.001% as a coloring agent.

TABLE 1

| Final concentration of each component for the preparation of test sample (TS) 1-5. | | | | | |
|---|---|---|---|---|---|
| Component | TS-1 | TS-2 | TS-3 | TS-4 | TS-5 |
| Sodium alginate | 0.175 w/v % | 0.175 w/v % | 0.175 w/v % | 0.175 w/v % | 2% w/v |
| Modifier xxy84 | 1 w/v % | 1 w/v % | 1 w/v % | 1 w/v % | 1 w/v % |
| Calcium chloride | 0.00 w/v % | 0.013 w/v % | 0.028 w/v % | 0.056 w/v % | 0.028 w/v % |

Example 2 Composition 2 Preparation

Test samples (TS) 6-10 were prepared by varying the ratio of sodium alginate (Kimica Corporation) as the Component (A) to modifier xxy84 (illustrated in Example 3) as the Component (B). The final concentration of each components is listed in the following Table 2. Specifically, in a suitable vessel, sodium alginate with or without modifier xxy84 were dissolved and continuously mixed in deionized water. Then, calcium chloride solution was added under stirring to obtain a homogeneous and viscous solution. Methylene blue may be added to TS 6-10 at a concentration of 0.001% as a coloring agent.

TABLE 2

| Final concentration of each component for the preparation of test sample (TS) 6-10. | | | | | |
|---|---|---|---|---|---|
| Component | TS-6 | TS-7 | TS-8 | TS-9 | TS-10 |
| Sodium alginate | 0.175% | 0.175% | 0.175% | 0.175% | 0.175% |
| Modifier xxy84 | 0 | 0 | 0.25% | 0.5% | 2% |
| Calcium chloride | 0 | 0.028 w/v % | 0.028 w/v % | 0.028 w/v % | 0.028 w/v % |

Example 3 Synthesis of Modifier

Modifier with varying ratio of hydrophobic diol (1,8-octanediol or polycaprolactone diols (PCL-500 or PCL- 1000)) to hydrophilic diol (polyethylene glycol (PEG) or β-glycerophosphate) were synthesized by reacting polycarboxylic acid with 1,8-octanediol or PCL-500 or PCL-1000 and PEG-200 and/or β-glycerophosphate according to Table 3 via a convenient one-pot polycondensation. Specifically, to synthesize the modifier, citric acid and different molar ratio of hydrophobic diols and hydrophilic diols were melted at 160° C. in a flask. The mixture was reacted at 145° C. under continuous stirring to prepare the prepolymer of xxy51, xxy75, xxy77, xxy82, xxy84, CPP-2, and CPP-4.

TABLE 3

Molar ratio of each monomer for the synthesis of modifiers.

| Monomer | xxy51 | xxy75 | xxy77 | xxy82 | xxy84 | CPP-2/-4 |
|---|---|---|---|---|---|---|
| polycarboxylic acid | 1 | 1 | 1 | 1 | 1 | 1 |
| Hydrophobic diols | 0.5 | 0 | 0.17 | 0.15 | 0.22 | 0.1 |
| Hydrophilic diols | 0.5 | 1 | 0.83 | 0.85 | 0.78 | 0.9 |

Example 4 Composition 3 Preparation

Test samples (TS) 11-13 were prepared by adding modifiers synthesized in Example 3, when preparing the composition according to Table 4. Specifically, in a suitable vessel, sodium alginate (Kimica Corporation), modifiers xxy77, xxy82, or xxy84, together with calcium chloride were dissolved and continuously mixed in deionized water under magnetic stirring to obtain a homogeneous and viscous solution. Methylene blue may be added to TS 11-13 at a concentration of 0.001% as a coloring agent.

TABLE 4

Final concentration of each component for the preparation of test sample (TS) 11-13.

| Component | TS-11 | TS-12 | TS-13 |
|---|---|---|---|
| Sodium alginate | 0.175% | 0.175% | 0.175% |
| Modifier | 1% xxy77 | 1% xxy82 | 1% xxy84 |
| Calcium chloride | 0.028 w/v % | 0.028 w/v % | 0.028 w/v % |

Example 5 Composition 4 Preparation

Test sample (TS) 14 with fluorescent agent Indocyanine green (ICG) added was prepared according to Table 5. Specifically, in a suitable vessel, sodium alginate (Kimica Corporation), modifier xxy84 and calcium chloride were dissolved and continuously mixed in deionized water under stirring to obtain a homogeneous and viscous solution. Next, ICG were added and rigorously mixed to generate a green coloring, strong fluorescent emission of which could be excited at wavelength between 600-850 nm.

TABLE 5

Final concentration of each component for the preparation of test sample (TS) 14.

| Component | TS-14 |
|---|---|
| Sodium alginate | 0.25% |
| Modifier xxy84 | 1% |
| Calcium chloride | 0.03% |
| Indocyanine green | 0.2% |

Example 6 Composition 5 Preparation

Test sample (TS) 15-17 were prepared according to Table 6. Specifically, in a suitable vessel, sodium alginate (Kimica Corporation), and calcium chloride were dissolved and continuously mixed in deionized water under stirring, followed by the addition and fully dissolution of poloxamer 188 (Fisher Scientific) to obtain a homogeneous and viscous solution.

TABLE 6

Final concentration of each component for the preparation of test sample (TS) 15-17.

| Component | TS-15 | TS-16 | TS-17 |
|---|---|---|---|
| Sodium alginate | 0.175% | 0.175% | 0.175% |
| Calcium chloride | 0.028% | 0.028% | 0.028% |
| Modifier Poloxamer 188 | 0.5% | 2% | 5% |

Example 7 Composition 6 Preparation

Test sample (TS) 18 and 19 were prepared according to Table 7. Specifically, in a suitable vessel, sodium alginate (Kimica Corporation), polyvinyl alcohol (PVA) at low molecular weight (Fisher scientific; average Mw 10,000-26,000 Da) and calcium tetraborate (calcium ions could mediate the crosslinking of sodium alginate while the brate ion would aid the complexing between PVA chains with abundant —OH groups) were fully dissolved and continuously mixed in deionized water overnight under stirring to obtain a homogeneous and viscous solution.

TABLE 7

Final concentration of each component for the preparation of test samples (TS) 18 and 19.

| Component | TS-18 | TS-19 |
|---|---|---|
| Sodium alginate | 0.3% | 0.3% |
| Modifier PVA | 0.1% | 0.4% |
| Calcium tetraborate | 0.028% | 0.028% |

Example 8 Composition 7 Preparation

Test sample (TS) 20-24 were prepared according to Table 8. Specifically, in a suitable vessel, sodium alginate (Kimica Corporation) with modifier xxy84/CPP-2/CPP-4 were fully dissolved and continuously mixed in deionized water. Then, calcium chloride solution was added under stirring to obtain a homogeneous and viscous solution. Methylene blue may be added to TS 20-24 at a concentration of 0.001% as a coloring agent.

TABLE 8

Final concentration of each component for the preparation of test sample (TS) 20-24.

| Component | TS-20 | TS-21 | TS-22 | TS-23 | TS-24 |
|---|---|---|---|---|---|
| Sodium alginate | 0.25% | 0.25% | 0.3% | 0.35% | 0.4% |
| Modifier xxy84 | 1% | 0 | 0 | 0 | 0 |
| Modifier CPP-2 | 0 | 1% | 1% | 0 | 0 |
| Modifier CPP-4 | 0 | 0 | 0 | 1% | 1% |
| Calcium chloride | 0.028% | 0.028% | 0.033% | 0.039% | 0.044% |

Example 9 Composition 8 Preparation

Test sample (TS) 20 were prepared according to Example 8. Then, test sample 20 solution with 0.001% methylene blue added was freeze-dried completely to obtain the composition in a form of lyophilized powder, which will be fully re-dissolved by adding water and continuous mixed via vertexing.

Example 10 Composition 9 Preparation

Test sample (TS) 25 was prepared according to Table 9. Specifically, in a suitable vessel, chitosan was first fully dissolved in 10 v/v % acetic acid and modifier containing β-glycerophosphate (xxy51) was dissolved in deionized water. Next, both chitosan and modifier were cooled down to 4° C., followed by adding the modifier solution dropwise to chitosan solution placed in an ice bath. 1 M of pre-cooled sodium bicarbonate was added to adjust solution pH to reach 7.2-7.4. Then, the mixture temperature was slowly brought up to 37° C. under rigorous and continuous stirring.

TABLE 9

Final concentration of each component for the preparation of test sample (TS) 25.

| Component | TS-25 |
|---|---|
| Chitosan | 1% |
| Modifier xxy51 | 1% |
| Sodium chloride | 0.5% |

Example 11 Composition 10 Preparation

Test sample (TS) 26 was prepared according to Table 10. Specifically, in a suitable vessel, gelatin (type B; low bloom) was dissolved in water at 60° C. while chitosan was dissolved in 1 v/v % acetic acid. Next, chitosan solution was added to gelatin solution at 60° C. and mixed thoroughly. Then, the mixture temperature was cooled down gradually to 4° C. under stirring, followed by adding 1 M of pre-cooled sodium bicarbonate to adjust solution pH to reach 7.2-7.4. Then, the mixture temperature was brought up to room temperature with sodium chloride added under rigorous and continuous stirring.

TABLE 10

Final concentration of each component for the preparation of Test Sample (TS) 26.

| Component | TS-26 |
|---|---|
| Gelatin | 2% |
| Modifier Chitosan | 0.5% |
| Sodium chloride | 0.5% |

Example 12 Injection Pressure Test

The injection pressure of test samples was measured using a standard endoscopic injector (Olympus, NM-400U-0423) with a 4 mm, 23-gauge needle, connected to a tube/catheter with a working length of 2300 mm and a channel size at 2.8 mm. The plastic syringes filled with the test samples prepared in Example 1 and Example 2 were placed on a syringe pump (New Era 9000) that is connected to the Olympus endoscopic injector and a pressure gauge through a 3-way Luerlock stopcock. With a pump rate of 5 mL/min, record the injection pressure reading on the pressure gauge when a steady solution flow through the endoscopic catheter and needle occurred. The test was carried out at room temperature.

TABLE 11

Injection pressure of test samples (TS)1-5.

| Test Sample | Injection pressure (psi) |
|---|---|
| TS-1 | 7.3 |
| TS-2 | 14.4 |
| TS-3 | 11.7 |
| TS-5 | 15.5 |

As shown in Table 11, it was obvious that when the modifier concentration remains constant, the injection pressure could be effectively adjusted by varying the ratio of sodium alginate (A) to calcium chloride (C). In addition, as shown in Table 12, the concentration of modifier xxy84 increased from 0% to 2%, the injection pressure was substantially decreased from 38 psi to 9.2 psi. The addition of modifier could evidently decrease the injection pressure of the corresponding compositions with the concentrations of SA and $Ca^{2+}$ unchanged.

TABLE 12

Injection pressure of selected test samples that are prepared by varying the modifier concentration.

| Test Sample | Injection pressure (psi) |
|---|---|
| TS-6 | 13.3 |
| TS-7 | 38.0 |
| TS-8 | 18.3 |
| TS-9 | 13.7 |
| TS-3 | 11.7 |
| TS-10 | 9.2 |

The injectability of the above test samples was also determined by hand manually using 10 mL syringe and standard endoscopic injector (Olympus, NM-400U-0423) with a needle diameter at 23 gauge, and a needle length of 4 mm, connected to a tube with a working length of 2300 mm and a channel size at 2.8 mm. An evaluation of the injectability of selected test samples is provided in Table 13. Commercially available sodium hyaluronate (HA) dissolved in deionized water at 0.4% and 0.24%, together with normal saline were also included as reference.

When the injection pressure reaches 40 psi or more, such as the 0.4% sodium hyaluronate (HA), it was difficult to inject by manually pushing the syringe piston with the hand, and the solution could only be injected out as a discontinuous flow instead of a steady continuous flow. It was consistent with what was reported in the art that the 0.4% HA at high molecular weight (between 1.5 and 3 million Da) usually is difficult to inject using endoscopic injectors, therefore requiring further dilution before injection. When the HA solution was diluted to be 0.24%, the injection pressure was 26.8 psi, which was close to the reported injection pressure value of commercially available HA solution (sigmaVisc™) in the art (21). As determined by hand, the 0.24% HA was slightly difficult to inject using an endoscopic injector but still was injectable, and the solution was able to be injected out continuously. As for test sample (TS) 6 and test sample (TS)16, their injection pressure was approximately 38 psi, and the solution was difficult to inject but still could be injected continuously through the endoscopic needle if pushed the syringe piston hard enough. Lastly, when the injection pressure was below 20 psi, such as the test sample (TS) 7, 4 and 3, the test samples were easily injected through the 23-gauge needle by manually pushing the syringe. More importantly, it was confirmed that the modifier (TS-10) was effective than poloxamer (TS-16) in terms of improving solution injectability.

Therefore, the injection pressure of the of example compositions, as measured according to the above method, can be tuned to values below 50 psi, such as values below 30 psi, and in some implementations values below 20 psi.

TABLE 13

Injectability of selected test samples determined manually by hand in comparison to that of sodium hyaluronate and saline controls.

| Test Sample | Injection pressure (psi) | Injectability as determined by hand |
|---|---|---|
| 0.4% sodium hyaluronate (HA) | 43.4 | Difficult to inject |
| 0.24% sodium hyaluronate (HA) | 26.8 | Slightly difficult but injectable |
| TS-6 | 38.0 | Difficult but injectable |
| TS-16 | 38.5 | Difficult but injectable |
| TS-7 | 18.3 | Easy to inject |
| TS-4 | 15.5 | Easy to inject |
| TS-3 | 11.7 | Easy to inject |
| Normal Saline | 1.6 | Easy to inject |

Example 13 Testing on Ex Vivo Porcine Stomach and Colon Specimens

Frozen porcine colon and stomach tissues were thawed in the water bath maintained at 37.0° C.±0.5° C., and then a 5 cm×5 cm square portion of the tissues was cut and stretched flat on an examination cork board with pins. Test sample (TS) 2, sterilized test sample (TS) 24, normal saline, and normal saline containing 0.001% Methylene blue was then injected into the submucosal layer of the resected square specimen of the porcine stomach/colon by means of a 5 mL syringe connected to a regular 25-gauge needle, and the injection volume was 1 mL±0.1 mL. As shown in FIG. 1, a more spherical and higher cushion with steep and clear edge was obtained by injecting 1 mL of TS-2 into colon tissues compared with that by injecting normal saline, and such a high cushion with clear edge would be of advantage to assist the subsequent resection procedure.

Figure 2:
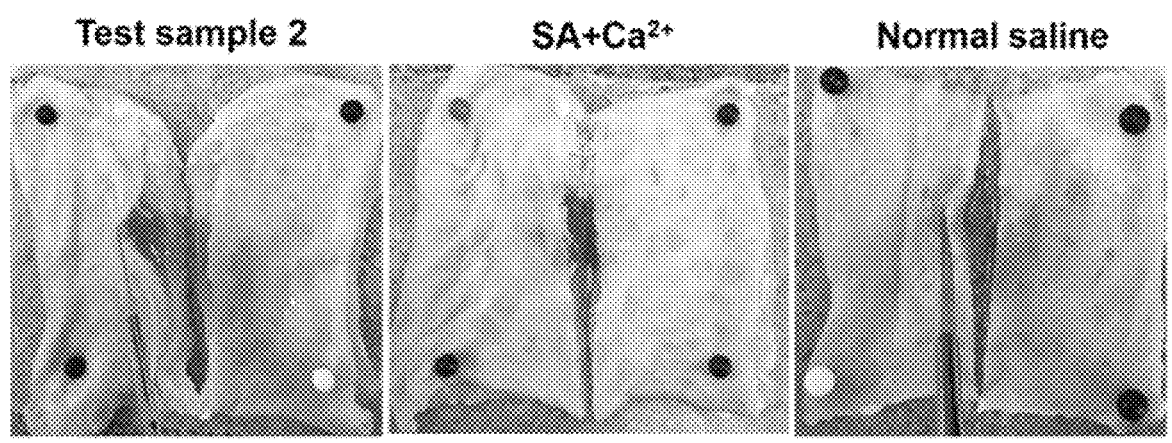
FIG. 2 illustrates formation of a thickened and less flowable product 15 mins after injection of test sample 2 (TS-2), calcium cross-linked sodium alginate fluid gels (SA+$Ca^{2+}$), and saline with 0.001% of Methylene blue added in the submucosal layer of colon sample.
Figure 3:
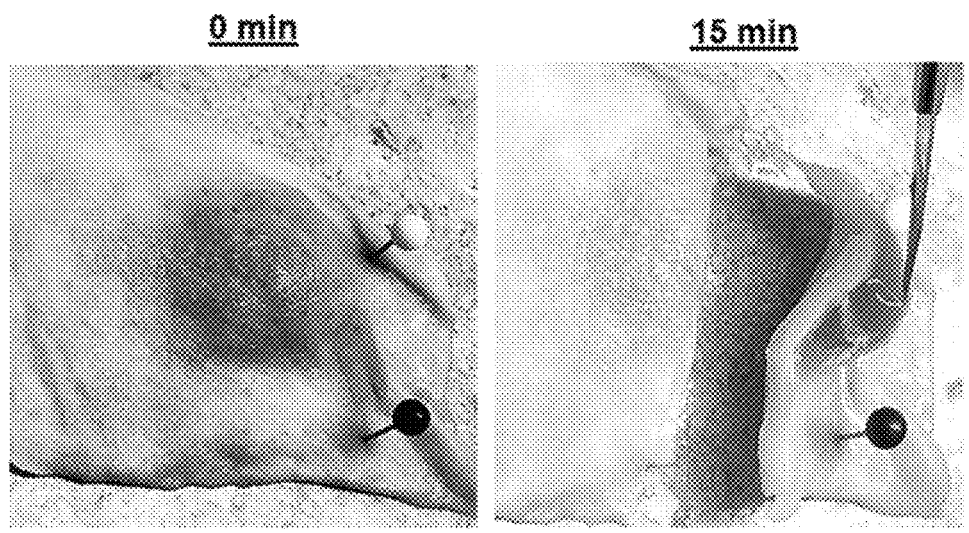
FIG. 3 illustrates formation of a thickened and less flowable product after injection of test sample 2 (TS-2) with 0.001% of Methylene blue added in the submucosal layer of porcine stomach sample.
Figure 4A:
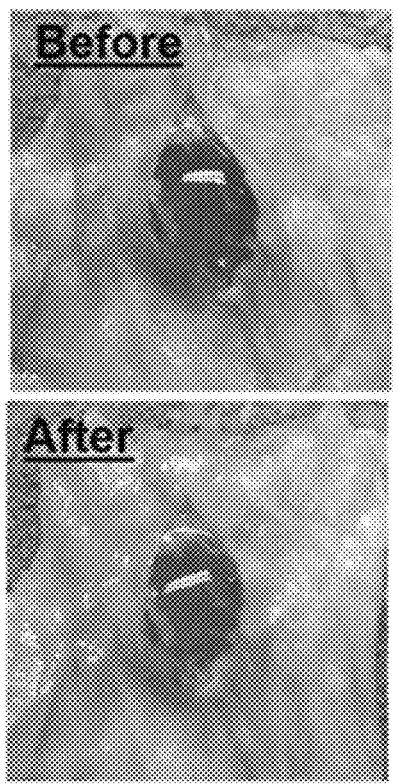
FIG. 4A illustrates the thickened and less flowable product obtained after injection of sterilized test sample 24 (TS-24) before and after flushed with 25 mL of normal saline.
Figure 4B:
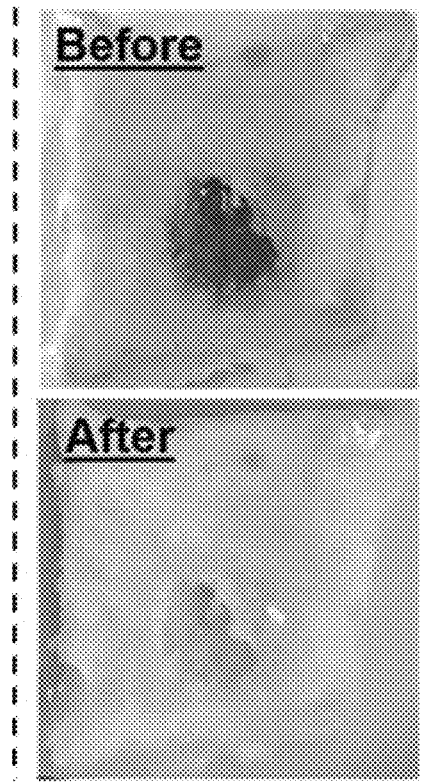
FIG. 4B illustrates the thickened and less flowable product disappeared after soaked in normal saline for 18 hours.

At the same time, TS-2 with 0.001% methylene blue added, together with ionically crosslinked sodium alginate fluid gels (0.175% SA+0.028 w/v % $Ca^{2+}$) and saline with the same amount of methylene blue were injected to better observe the cushion morphology and the product formed in the submucosal layer. 15 min after injection of the test samples, the submucosal cushion was cut open with a scalpel, and the final blue product held in the submucosal layer was observed. As shown in FIG. 2, it was surprisingly to find out that TS-2 in a flowable state before injection, formed a blue cushion displaying a thickened and less flowable state, which was held in the submucosal space of the colon tissue. Ionically crosslinked sodium alginate fluid gels after injection also formed a similar thickened cushion, and in comparison, saline leaked out of the submucosal space immediately once the cushion was cut open. Also, a more confined edge of the blue cushion could be observed by using TS-2 and sodium alginate fluid gels, in comparison to that in the saline group which displayed a more dissipated pattern. The cushion in a favored spherical shape with steep and clear margin was also observed after injected to the porcine stomach tissue (FIG. 3), and more importantly, after 15 mins, the injected TS-2 consistently formed thickened and less flowable product in the submucosal space, which is believed to favor durable and prolonged elevation. In addition, the injection of sterilized TS-24 into the colon tissue also formed a thickened gel product, as displayed in FIG. 4A after the cushion was cut open. After the gel product was flushed with 25 mL of saline using standard endoscopic needle, the majority of the blue cushion remained at the resection site covering the dissected wound, but the gel completely dissipated after being soaked in saline for 18 hours (FIG. 4B). It indicated the capability of the formed thickened product to resist passive diffusion upon flushing and provide a relatively stable wound protection.

Example 14 Elevation Duration Test

Frozen colon tissues were thawed in the water bath maintained at 37.0° C.±0.5° C., and then a 5 cm×5 cm square portion of the tissues was cut and stretched flat on an examination cork board with pins. Test samples, normal saline and 0.4% sodium hyaluronate solution (HA; ACROS Organics; Mw: 1,700,000 Da) were then injected into the submucosal layer of the porcine colon, respectively, by means of a 5 mL syringe connected to a regular 25-gauge needle, and the injection volume was 1 mL±0.1 mL. After injection, the needle is removed from the specimen. The morphology and initial height of the formed submucosal cushions and the changes in heights were recorded post-injection at 5, 10, 15, 20 or 30, 45, 60, 75 and 90 mins.

Figure 5:
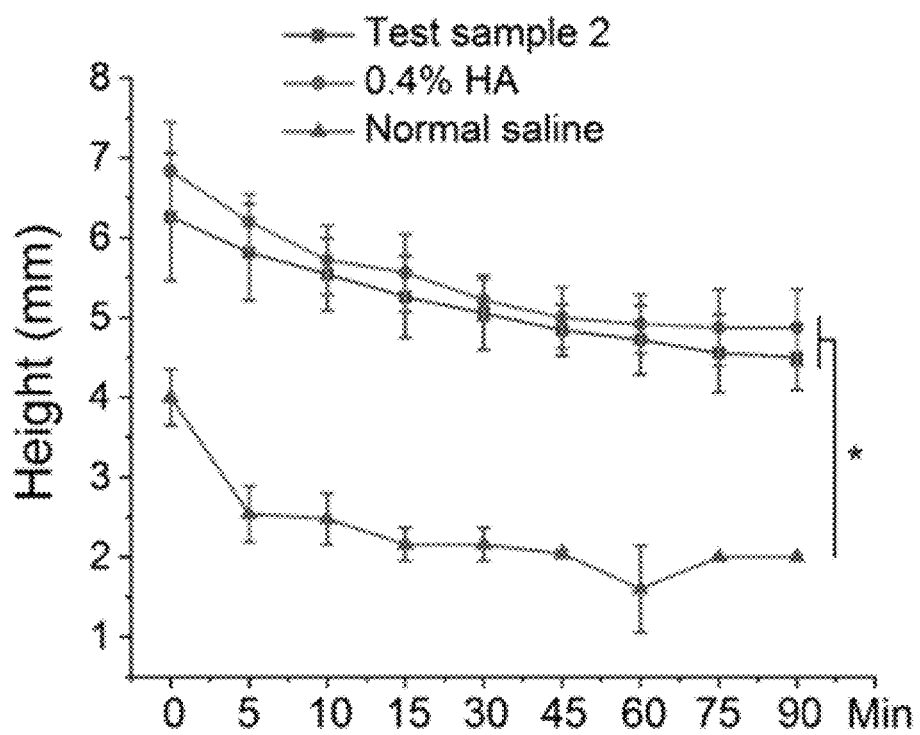
FIG. 5 illustrates the elevation duration of test sample 2 (TS-2) as compared to that of 0.4% sodium hyaluronate (HA) and normal saline for up to 90 minutes after injected into the submucosal layer of colon tissues.

It can be observed in FIG. 2 that test sample (TS) 2 initially in a flowable state could produce thickened less flowable product after injected into the confined submucosal layer of colon tissues. Surprisingly, TS-2 with an injection pressure of 14.4 psi generated submucosal cushions with an elevation height and a 90 mins elevation duration that are comparable to that of 0.4% HA with a much higher injection pressure of 43.4 psi (FIG. 5). The initial height and duration of the cushion generated by both TS-2 and 0.4% HA were also evidently superior to that using normal saline. The comparable elevation performance of TS-2, while with substantially lowered injection pressure as compared to 0.4% HA, are of great advantage, especially for endoscopic submucosal injection applications.

In addition, how modifiers with different ratios of hydrophobic to hydrophilic diols could affect submucosal elevation was also evaluated, the result of which is shown in Table 14. It turned out that an increase in the ratio of hydrophobic 1,8-octanediol, such as xxy84 (TS-13), or an usage of hydrophobic diols of longer chains, such as CPP-2 (TS-21), in the modifier's composition effectively improved the initial elevation height and the duration of the generated cushion, as compared to that of for example, TS-11 and 12.

It is probably because that the increased hydrophobicity in the composition helps to prevent the dissipation of water molecule within the cushion towards surrounding tissues.

Figure 6A:
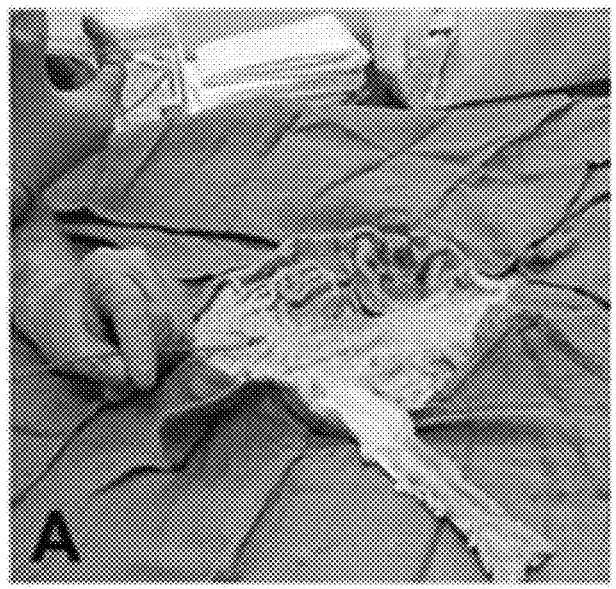
FIG. 6A illustrates ex vivo injection of test sample 21 (TS-21) for submucosal lift on fresh porcine tissues using endoscopic needles.
Figures 6B, 6C, 6D, 6E, 6F, 6G:
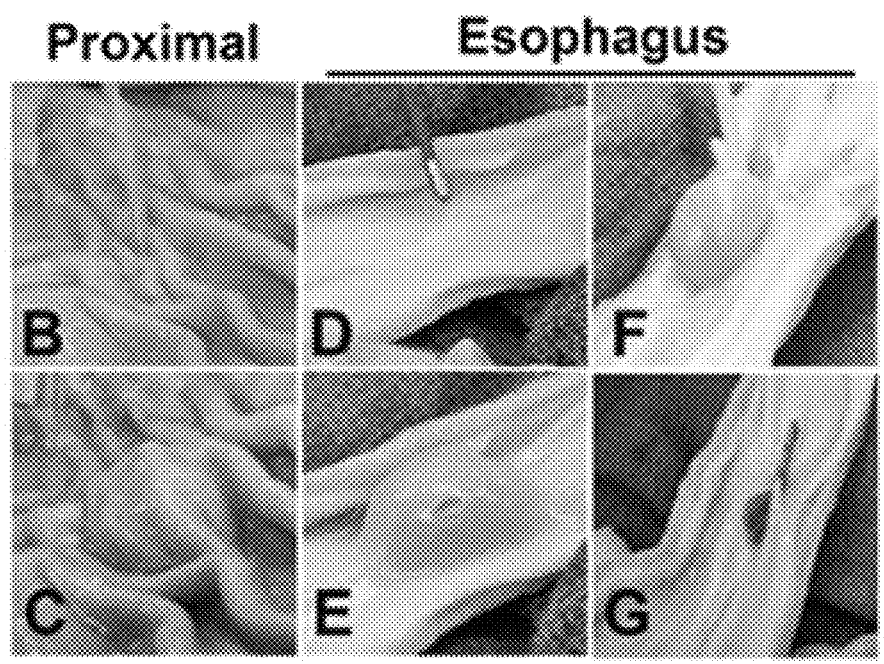
FIG. 6B depicts images of the submucosal cushion formed before injection into proximal stomach.
FIG. 6C depicts images after injection into proximal stomach.
FIGS. 6D and 6E depict images of the submucosal cushion formed before and after, respectively, the injection into esophagus.
FIG. 6F depicts an image of an esophagus cushion with an endoscopic snare applied.
FIG. 6G depicts an image of an esophagus wound partly closed by clips after resection.

The feasibility of injecting TS-21 into freshly recovered porcine gastrointestinal (GI) tissues including both esophagus and proximal stomach for submucosal lift using endoscopic needles has been demonstrated. As shown in FIG. 6, 2 mL of TS-21 successfully generated preferred submucosal cushions on both proximal stomach and on esophagus tissues. A snare could be easily placed on the formed cushion. After resection, the remaining materials did not impede the closure of the resection site using endoscopic clips.

TABLE 14

The height of the cushion that formed on ex vivo colon tissues after injection of 1 mL test samples.

| Test sample | Elevation height after injection (mm) | | |
|---|---|---|---|
| | 0 min | 15 min | 20 min |
| TS-11 containing xxy77 | 5 | 4 | 3.5 |
| TS-12 containing xxy82 | 5 | 4 | 3.5 |
| TS-13 containing xxy84 | 6 | 5.5 | 5 |
| TS-21 containing CPP_2 | 7 | 6.3 | 5.8 |

Example 15 Rheology and Apparent Viscosity Tests

Figure 7:
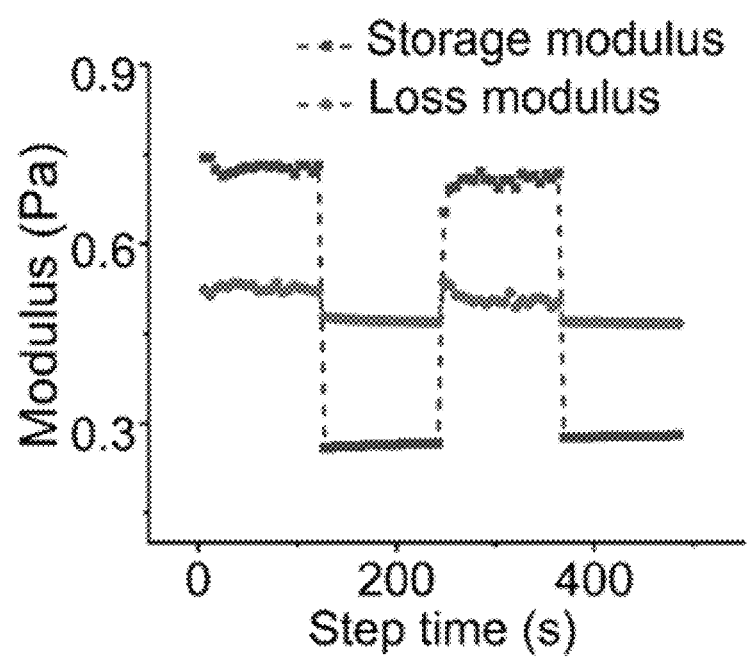
FIG. 7 depicts example data demonstrating recoverable shear-thinning profile of test sample 22 (TS-22).

To understand the rheological behavior, step-strain measurement of test sample (TS) 22 was performed using a TA Instrument's Discovery series rheometer with 60 mm plate geometry. The test started at 6.3 rad s$^{-1}$ via application of low stain at 1% for 2 min. The shear thinning was induced via application of 300% strain for 2 min. Then the strain is released to 1% for 2 min to allow the fluid gel to recover. As a result (FIG. 7), TS-22 in forms of fluid gels behaved like gel at low strain (1%), and the storage moduli decreased abruptly with the increase of strain displaying a liquid behavior, due to the disruption of inter-particle interactions and a greater degree of particle orientation with the increasing shear stress. A quick recovery of storage moduli was observed with the strain lowered from 300% to 1%, resulting from the recovery of the interparticle interactions (liquid behavior: storage moduli<loss moduli; solid behavior: storage moduli>loss moduli).

Figure 8:
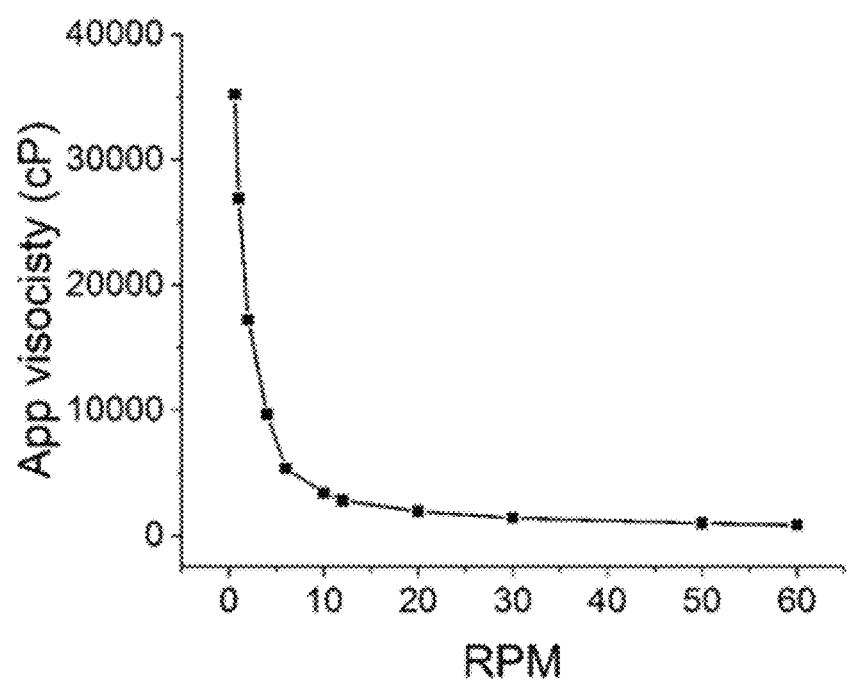
FIG. 8 depicts an example shear-thinning curve of test sample 23 (TS-23).

The shear-thinning property of the fluid gel composition was further confirmed by testing the apparent viscosity of the fluid gel composition using a Brookfield rotary viscometer. Specifically, appropriate amount of TS-23 was loaded to the viscometer, and the test started by initiating the rotation of spindle and the apparent viscosity and torque readings were recorded. The rotational speed was then increased in steps, and the viscosity and torque reading at each speed were recorded. After the test completed, a shear-thinning graph of viscosity versus rotational speed was plotted and the shear-thinning index could be determined by dividing the apparent viscosity at a low rotational speed by the viscosity at a speed 10-times higher, according to ASTM D2196. Typical speed combinations are 0.6 and 6 rpm, 6 and 60 rpm, 10 and 100 rpm. The resultant viscosity ratio is an index of the degree of shear thinning over that range of rotational speed with higher ratios indicating greater shear thinning. FIG. 8 displayed a typical shear-thinning behavior of TS-23, where an increase in rotational speed led to an abrupt decrease in apparent viscosity. It is a much-desired property for endoscopic injection applications. Moreover, the shear thinning index of TS-23 was determined to be in a range of 6.28-8.9.

Example 16 Microscopic Images of the Gelled Particles

Figure 9:
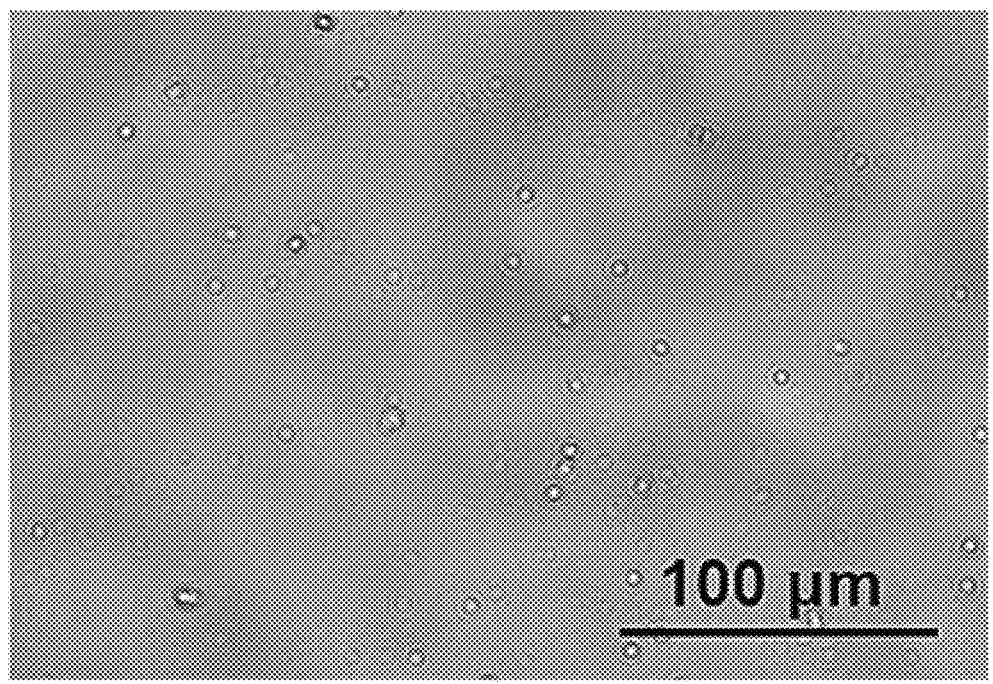
FIG. 9 depicts example microscopic images of the gelled particles in sterilized test sample 23 (TS-23).

Optical microscope was utilized to observe the suspended gelled particles in sterilized TS-23, to confirm the formation of gelled particles in the fluid gel composition. As shown in FIG. 9, the generated gelled particles in sterilized TS-23 were observed to be mostly spherical with a high degree of isotropy.

Example 17 Cytotoxicity Test

The in vitro cytotoxicity to L929 cells caused by direct contact of test sample (TS)-3 as a representative formulation was evaluated according to ISO 10993-5. Specifically, filter discs (Fisher scientific; Ap2501000; d=1 cm, surface area=0.785 cm$^2$) were soaked thoroughly in Test sample-3 solution or DI water to absorb the test samples or DI water. Next, the filter discs were placed on top of a sub-confluent layer (>80% confluency) of L929 cells that cultured in 12 well plates to get direct contact between test samples and beneath cells. After 24 hours, the filter discs were removed, and the cell viability was measured by cell counting kit (CCK)-8 according to the manufacturers' instructions.

Figure 10:
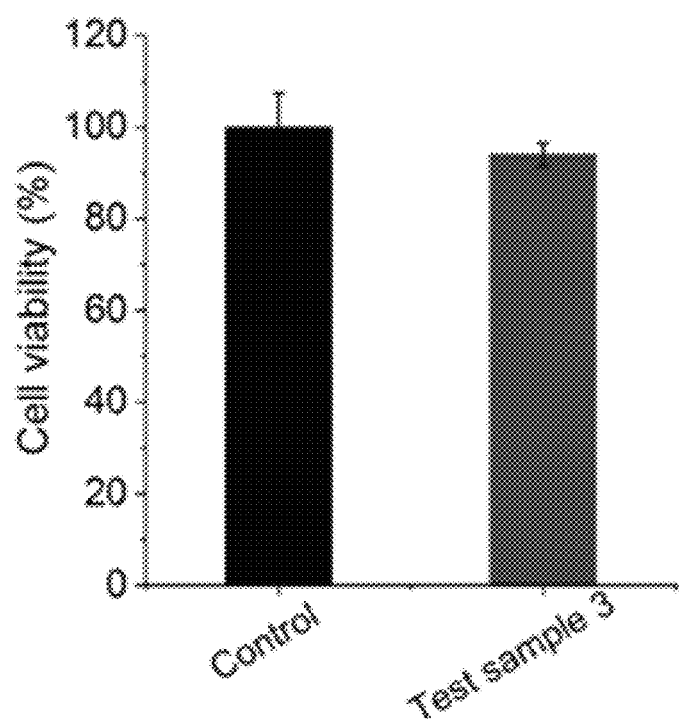
FIG. 10 depicts an example cytotoxicity evaluation of the direct contact of test sample 3 (TS-3).

As shown in FIG. 10, the reduction of cell viability after direct contact with test sample-3 for 24 h is 6%, less than 30%, therefore, test sample-3 is considered as non-cytotoxic.

Example 18 Hemostatic Test

The hemostatic property of the test samples was evaluated by a whole blood clotting assay. To determine the clotting time, the clotting reaction was activated with the addition of 1 mL of 0.1 M calcium chloride (CaCl$_2$) to 10 mL citrated blood. After vertexing for 10 s, 100 µL blood sample was added to 48 well plates with 10 µL sample solution per well. At the selected time points (3, 4, 5, 6, 7, and 8 mins), each well was washed with PBS to halt clotting. The clot was then washed repeatedly until the solution turned clear. The final clotting time was defined as when a uniform clot was formed in the well with no change in clot size in subsequent wells.

The whole blood clotting assay was also performed by spectrophotometrically measuring the relative absorbance of blood samples. In 2 mL centrifuge tubes, 20 µL of sterilized TS-24 and 200 µL of citrated bovine blood were added and mixed together. The clotting reaction was activated with the addition of 20 µL of 0.1 M calcium chloride (CaCl$_2$) to the tube and vortexed for 10 s. At the selected time points (6, 8, 10, 12, 14, 16, and 18 min), 1 mL of DI water was added to the corresponding tube to lyse the red blood cells that are not trapped in the clot. Next, 200 µL of solution was transferred to 96 well plates and was measured at 540 nm.

Figure 11A:
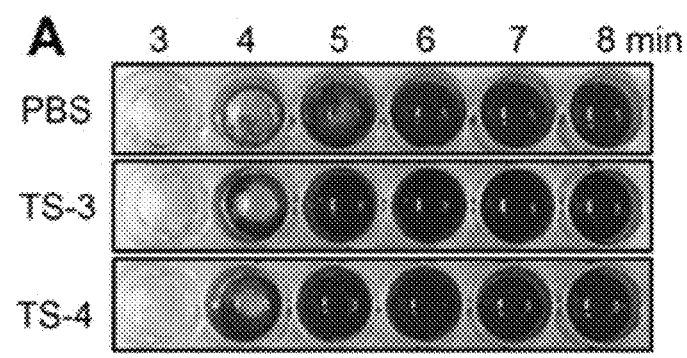
FIGS. 11A and 11B depict example data illustrating whole blood clotting time of test samples 3 and 4 (TS-3 and TS-4) in comparison to PBS.
Figure 11B:
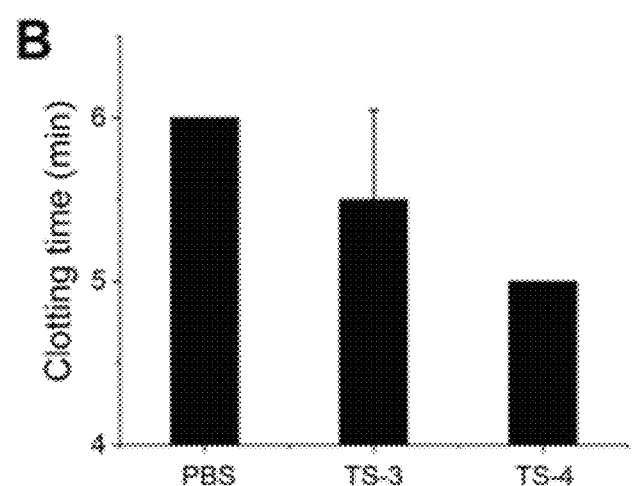
Figure 12:
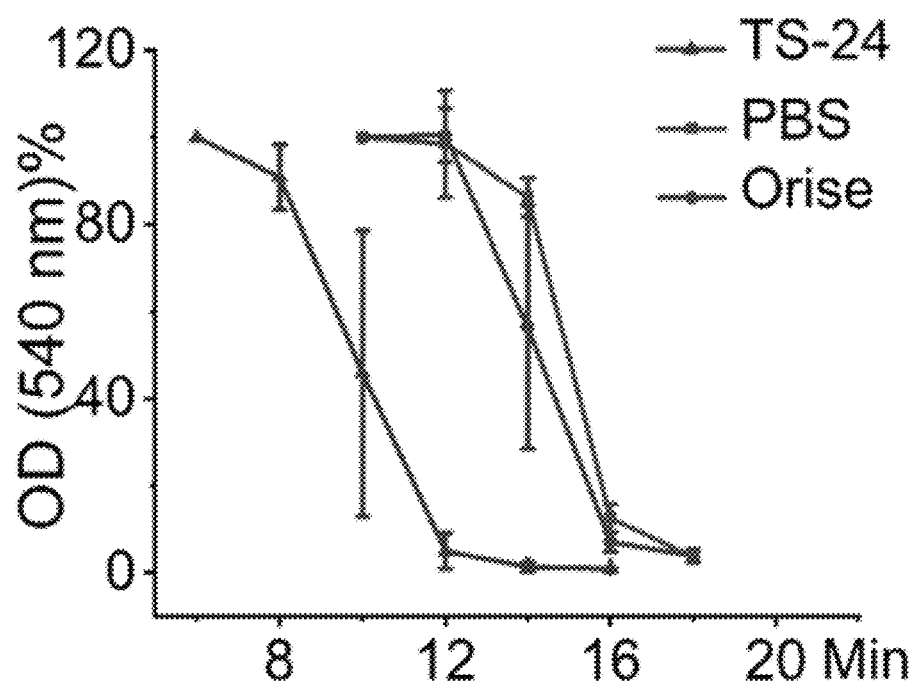
FIG. 12 depicts example hemostatic properties of the sterilized test sample 24 (TS-24) in comparison to that of PBS and commercially available Orise Gel submucosal lifting agent (n=4).

According to FIG. 11, the clotting time of the control group with only PBS added was 6 min, and the addition of TS-3 brought forward the clotting time to be around 5.5 min. Moreover, by increasing the calcium ion concentration in the composition, for example, by doubling the calcium concentration of test sample 3, the blood clotting of test sample 4 was further accelerated to complete at 5 min. Consistently, after lysed the red blood cells, it was found that TS-24 after sterilization induced accelerated blood clotting at all time points as compared with the Orise gel and PBS control groups (FIG. 12), supporting the notion that the composition provided in the present disclosure displayed hemostatic properties that may favor blood control during or after the resection procedure.

The invention claimed is:

1. A shear-thinning fluid gel composition comprising:
a gelling agent,
a salt,
a modifier, and
water,
wherein the gelling agent, the modifier, the salt or a combination thereof displays hemostatic function, and
wherein the gelling agent comprises alginate, and
wherein said modifier reduces the injection pressure of the composition, and
wherein said modifier comprises a hydrophilic polymer, an amphiphilic polymer, or both, and
wherein the hydrophilic polymer comprises a hydrophilic synthetic polyester, and
wherein the amphiphilic polymer comprises an amphiphilic synthetic polyester,
wherein the modifier bridges between gelling agent chains, and
wherein the fluid gel composition comprises a suspension of gelled particles.

2. The composition according to claim 1, wherein said composition is prepared by mixing the gelling agent, the salt, the modifier, and water under continuous stirring.

3. The composition according to claim 1, wherein said composition has an injection pressure below 50 psi.

4. The composition according to claim 1, wherein said composition has a shear-thinning index between 1 and 20.

5. The composition according to claim 4, wherein said composition has a shear-thinning index between 2 and 12.

6. The composition according to claim 1, wherein said gelling agent further comprises, in addition to the alginate, at least one polysaccharide or at least one protein, wherein
the at least one polysaccharide is xanthan gum, k-carrageenan, gellan gum, guar gum, locust bean gum, pectin, carboxymethyl starch, hydroxyethyl starch, chitosan, agarose, or a combination thereof, and wherein
the at least one protein is whey protein, gelatin, or both.

7. The composition according to claim 6, wherein said at least one polysaccharide is chitosan, or wherein said at least one protein is gelatin.

8. The composition according to claim 1, wherein said gelling agent is present at a concentration between 0.05 to 6.5 w/v %.

9. The composition according to claim 1, wherein said hydrophilic synthetic polyester is prepared by reacting a polycarboxylic acid (PCA) with at least one hydrophilic diol (DPHO) selected from a group consisting of: 1,4-butanediol, 1,6-hexanediol, poly (ethylene glycol) (PEG), 1,2-propanediol-sebacate, poly(vinyl alcohol) or any combination thereof, and wherein said hydrophilic synthetic polyester has a molecular weight ranging from 500 to 20,000 Da.

10. The composition according to claim 1, wherein said amphiphilic synthetic polyester is prepared by reacting a polycarboxylic acid (PCA) with at least one hydrophobic diol (DPHO) selected from a group consisting of: 1,8-octanediol, poly(propylene glycol) (PPG), polycaprolactone (PCL) diol or polylactide (PLA) diols, and at least one hydrophilic diol (DPHO) selected from a group consisting of: 1,4-butanediol, 1,6-hexanediol, poly (ethylene glycol) (PEG), 1,2-propanediol-sebacate, poly(vinyl alcohol), or a combination thereof, and wherein said amphiphilic synthetic polyester has a molecular weight ranging from 500 to 20,000 Da.

11. The composition according to claim 10, where said polycarboxylic acid comprises at least one of the following: aconitic acid, propane-1,2,3-tricarboxylic acid, agaric acid, citric acid, isocitric acid, trimesic acid, furantetracarboxylic acid, biphenyl-3,3',5,5'-tetracarboxylic acid, bi(cyclopropane)-2,2',3,3'-tetracarboxylic acid, 1,2,3,4-butanetetracarboxylic acid, 1,2,3,4-cyclobutanetetracarboxylic acid, (+)-(18-crown-6)-2,3,11,12-tetracarboxylic acid or a combination thereof.

12. The composition according to claim 1, wherein said modifier is present at a concentration below 10 w/v %.

13. The composition according to claim 12, wherein said modifier is present at a concentration between 0.25% and 5 w/v %.

14. The composition according to claim 1, wherein said salt comprises one or more of a monovalent, a divalent, a multivalent cation or anion that is compatible with said gelling agent.

15. The composition according to claim 1, wherein said salt comprises a sodium salt, a calcium salt or both.

16. The composition according to claim 15, wherein said sodium salt comprises sodium chloride, sodium bicarbonate, sodium phosphate dibasic, sodium sulfate, sodium gluconate, sodium lactate, sodium citrate, or sodium glycerophosphate, and wherein said calcium salt comprises calcium chloride, calcium lactate, calcium gluconate, calcium tetraborate, calcium citrate, calcium sulfate, calcium glycerophosphate, or dibasic calcium phosphate.

17. The composition according to claim 16, wherein said salt comprises calcium chloride having a concentration between 0.01 and 0.4 w/v %.

18. The composition according to claim 1, wherein said salt is present at concentrations below 0.9 w/v %.

19. The composition according to claim 1, wherein said composition further comprises a coloring agent.

20. The composition according to claim 19, wherein said coloring agent comprises methylene blue, indigo carmine, lugol iodine, indocyanine green, toluidine blue, cresyl violet, congo red, phenol red, or a combination thereof.

21. The composition according to claim 1, wherein said composition further comprises one or more of: a photoluminescent agent, a preservative, a defoamer, a stabilizer, an antioxidant, a photosensitizer, a therapeutic agent, or a combination thereof.

22. The composition according to claim 21, wherein the composition comprises at least the photoluminescent agent, wherein the photoluminescent agent is a xanthene derivative, a cyanine derivative, a quantum dot, a zinc sulfide, a strontium aluminate, or a small molecule fluorescent dye, and wherein the small molecule fluorescent dye is made by reacting citric acid with an amine-containing compound.

23. The composition according to claim 1, wherein said composition is injectable through a needle, and wherein the needle is a commercially available endoscopic needle.

24. A method of using a composition in an endoscopic procedure, the method comprising:
administering the composition of claim 1 to a target tissue in a human to provide tissue elevation and hemostatic function.

25. The method of claim 24, wherein administering the composition is performed using an endoscopic injection needle having a needle diameter at gauge from 21 to 26.

26. The composition according to claim 1, wherein said alginate comprises sodium alginate and the sodium alginate has a viscosity of 5 to 1500 cP at 1 w/v % and 20° C.

27. The composition according to claim 26, wherein the sodium alginate has a viscosity of 100 to 700 cP at 1 w/v % and 20° C.

28. The composition according to claim 26, wherein the sodium alginate has a viscosity of 300 to 600 cP at 1 w/v % and 20° C.

29. The composition according to claim 1, wherein said modifier increases tissue elevation of the composition.

30. The composition according to claim 1, wherein the salt comprises calcium chloride.

* * * * *